United States Patent [19]

Pfeiffer et al.

[11] 4,426,371
[45] Jan. 17, 1984

[54] NOVEL N-HYDROXYALKYLATED DICARBOXYLIC ACID BIS(3,5-DICARBAMOYL-2,4,6-TRIIODOANILIDES), AS X-RAY CONTRAST MEDIA

[75] Inventors: Heinrich Pfeiffer; Ulrich Speck, both of Berlin, Fed. Rep. of Germany

[73] Assignee: Schering, Aktiengesellschaft, Berlin and Bergkamen, Fed. Rep. of Germany

[21] Appl. No.: 292,115

[22] Filed: Aug. 12, 1981

[30] Foreign Application Priority Data

Oct. 10, 1980 [DE] Fed. Rep. of Germany ....... 3038853

[51] Int. Cl.³ .................... A61K 49/04; A61K 31/165
[52] U.S. Cl. ........................................ 424/5; 424/324; 564/153
[58] Field of Search ..................... 564/153; 424/5, 324

[56] References Cited

U.S. PATENT DOCUMENTS

| | | | |
|---|---|---|---|
| 3,701,771 | 10/1972 | Almen et al. | 564/153 |
| 4,001,323 | 1/1977 | Felder et al. | 564/153 |
| 4,021,481 | 5/1977 | Almen et al. | 564/153 |
| 4,062,934 | 12/1977 | Tilly et al. | 564/153 |
| 4,230,845 | 10/1980 | Smith | 564/153 |
| 4,250,113 | 2/1981 | Nordal et al. | 564/153 |
| 4,283,381 | 8/1981 | Speck et al. | 564/153 |

Primary Examiner—David M. Naff
Assistant Examiner—Frederick W. Pepper
Attorney, Agent, or Firm—Millen & White

[57] ABSTRACT

Novel N-hydroxyalkylated dicarboxylic acid bis(3,5-dicarbamoyl-2,4,6-triiodoanilides) have Formula I

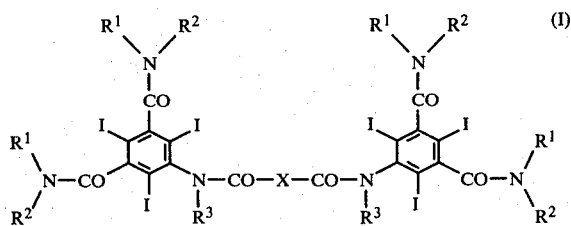

wherein
$R^1$ is a lower, linear or branched mono- or polyhydroxyalkyl residue,
$R^2$ is hydrogen, lower alkyl, or $R^1$,
$R^3$ is lower mono- or dihydroxyalkyl, and
X is a direct bond or linear or branched alkylene, which can be interrupted by one or more oxygen atoms or substituted by hydroxy or alkoxy groups.

The novel dimeric compounds of Formula I possess good pharmacological and physicochemical properties making them very advantageous as radiopaque agents in all fields of application for water-soluble, iodine-containing X-ray contrast media.

19 Claims, No Drawings

NOVEL N-HYDROXYALKYLATED DICARBOXYLIC ACID BIS(3,5-DICARBAMOYL-2,4,6-TRIIODOANILIDES), AS X-RAY CONTRAST MEDIA

BACKGROUND OF THE INVENTION

For X-ray diagnostic testing, for example concerning the organs of the urinary tract and the vessels visualized by angiography, compatible salts of 2,4-6-triiodobenzoic acids have been developed as contrast media. These compounds, however, are not tolerated by the organism without side effects at relatively high dosages, although their toxicity is frequently minor. An adequate visualization of the vascular system, the urinary tract system, as well as the cerebrospinal cavities and other systems requires the use of high dosages of contrast media, or highly concentrated solutions. Consequently, the physicochemical properties of the contrast media and their solutions have high significance. Important pharmacological effects, such as pain, blood pressure declines, vascular damage, and many others are attributed to such properties.

Compared with the salts of triiodinated benzoic acid derivatives, water-soluble nonionic compounds exhibit a series of advantages. For example they have a lower osmotic pressure, thus causing less pain and lesser damage to the endothelium in angiography. Furthermore, their urine concentration is higher and, for subarachnoid injection, arachnoiditis is less frequently encountered. In myelography, a lower tendency toward convulsions (epileptogenicity) has been observed using the nonionic X-ray contrast media. However, it has not been possible to prepare solutions sufficiently concentrated and radiopaque for use in angiography and myelography using these compounds, including, for example, metrizamide or iopamidol, which solutions are not hypertonic with respect to the blood or other body fluid.

Compatible, hexaiodinated and nonionic X-ray contrast media from which highly concentrated and blood-isotonic, aqueous solutions can be prepared were described for the first time in DOS [German Unexamined Laid-Open Application] No. 2,628,517 (U.S. Pat. No. 4,239,747). Similar compounds have also been disclosed in DOS No. 2,805,928 (U.S. Pat. No. 4,139,605).

Although nonionic hexaiodinated X-ray contrast media are rather well compatible on account of their advantageous physicochemical properties (especially strong hydrophilicity and low osmotic pressure), the results attained with the compounds described thus far have not as yet been fully satisfactory. For example, one disadvantage is the high viscosity of precisely the compounds having high compatibility and ready solubility and/or the low solubility of less viscous compounds with a high iodine content, as well as certain toxic effects upon intravenous administration of several of the heretofore disclosed compounds in spite of relatively high $LD_{50}$ values.

SUMMARY OF THE INVENTION

Accordingly, it is an object of this invention to provide new compounds suitable for use as non-ionic contrast media which ameloirate or overcome the foregoing disadvantages.

Upon further study of the specification and appended claims, further objects and advantages of this invention will become apparent to those skilled in the art.

These objects have been achieved by this invention by providing novel N-hydroxyalkylated dicarboxylic acid bis(3,5-dicarbamoyl-2,4,6-triiodoanilides) of the formula

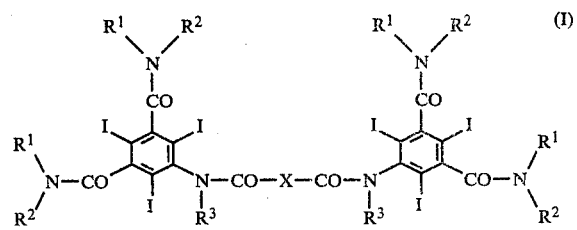

wherein
$R^1$ is lower, linear or branched mono- or polyhydroxyalkyl,
$R^2$ is hydrogen, lower alkyl, or $R^1$,
$R^3$ is 2-hydroxyethyl or 2,3-dihydroxypropyl, and
X is a direct bond or a linear or branched alkylene, which can be interrupted by one or more oxygen atoms or substituted by hydroxy or alkoxy.

This invention also provides a process for the preparation of such compounds and novel X-ray contrast media containing them as radiopaque agents.

DETAILED DISCUSSION

With respect to the definition of $R^1$, $R^2$ and X, the disclosure of U.S. Pat. No. 4,239,747 is incorporated by reference herein, unless contradicted herein.

The residue $R^1$ contains, as the linear or branched lower mono- or polyhydroxyalkyl residue, 2-8 carbon atoms, preferably 2-5 carbon atoms. Straight-chain residues of $R^1$ consist preferably of 2-4 carbon atoms, branched residues preferably of 3-5 carbon atoms. The hydroxy groups in $R^1$ can be primary and/or secondary and are not present in the α-position. The residue $R^1$ can contain 1-5 hydroxy groups, 1-3 hydroxy groups being preferred. Thus, compounds of Formula I can contain in the $R^1$ groups in total 4-40 hydroxy groups, preferably 4-24 hydroxy groups. Examples of residues $R^1$ include: 2-hydroxyethyl, 2-hydroxypropyl, 3-hydroxypropyl, 2,3-dihydroxypropyl, 2,3-dihydroxybutyl, 2,4-dihydroxybutyl, 3,4-dihydroxybutyl, 3-hydroxy-2-(hydroxymethyl)propyl, 2,3-dihydroxy-1-methylpropyl, 2-hydroxy-3-(hydroxymethyl)butyl, 2,3,4-trihydroxybutyl, 2,4-dihydroxy-3-(hydroxymethyl)butyl, 3-hydroxy-2,2-bis(hydroxymethyl)propyl, 4-hydroxy-3,3-bis(hydroxymethyl)butyl, 4-hydroxy-2,2-bis(hydroxymethyl)butyl, 2-hydroxy-1,1-bis(hydroxymethyl)ethyl, 1,3-dihydroxyisopropyl, 2,3-dihydroxy-1-hydroxymethylpropyl, etc.

When $R^2$ is lower alkyl, preferred are straight-chain residues of 1-4 carbon atoms, most preferably 1-2 carbon atoms, such as, for example, butyl, propyl, ethyl, and especially methyl. For $R^2=R^1$, the above discussion applies.

X is straight-chain or branched alkylene of 1-6 C-atoms which can be interrupted by one or more oxygen atoms, preferably 1-4 such atoms. A straight-chain alkylene of 1-4 carbon atoms is preferred, which also can be interrupted by one or more, preferably by one, two, or also three oxygen atoms. The oxa atoms are separated from each other by at least two methylene and from the ends of the alkylene by at least one methylene. Examples in this connection are: —CH$_2$—, —(CH$_2$)$_4$—, —(CH$_2$—CH$_2$—O—CH$_2$—CH$_2$)—, —(CH$_2$—O—CH$_2$)$_2$—, and —(CH$_2$—O—CH$_2$)$_3$—.

Branched-chain residues X include:

—[CH$_2$—C(CH$_3$)$_2$—CH$_2$]—, —[CH$_2$—CH(CH$_3$)—CH$_2$—CH$_2$]—,

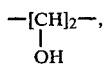

and similar residues.

X as straight-chain or branched alkylene can also be substituted by C$_1$–C$_2$-alkoxy groups, wherein methoxy or ethoxy groups are preferred. Generally, 1–4 alkoxy and 1–4 hydroxy substituents are possible.

It was surprising that, per this invention, a comparatively minor chemical modification of the class of compounds described in DOS No. 2,628,517 (U.S. Pat. No. 4,239,747) would lead to a significant improvement in compatibility and to an increase in solubility. This can be seen from Table I wherein the compound A of this invention (malonic acid bis[3,5-bis(1,3-dihydroxyisopropylcarbamoyl)-2,4,6-triiodo-N-2-hydroxyethylanilide]) is compared with respect to osmotic pressure, viscosity, and compatibility with oxalic acid bis[3,5-bis(2,3-dihydroxypropyl-N-methylcarbamoyl)-2,4,6-triiodo-anilide] (B), as well as with iopamidol (5-[α-hydroxypropionyl-amino]-2,4,6-triiodoisopthalic acid bis[1,3-dihydroxyisopropyl-amide]) and metrizamide [2-(3-acetamido-2,4,6-triiodo-5-[N-methylacetamido]-benzamido)-2-deoxy-D-glucose)].

The extraordinarily high compatibility of the compounds of this invention is remarkable, as can be seen from the extremely high LD$_{50}$ value of the table. An examination of the animals subjected to the test showed a reduced renal toxicity as compared with the comparison compounds which, at this high dose, is a very essential criterion. The compounds prepared according to this invention are furthermore isotonic with the blood in the concentration of, e.g., 300 mg iodine/ml customary for angiography; due to their viscosity, they are suitable for rapid injection as well as for injection through fine needles.

The compounds of this invention are thus excellently suitable as opacifying compounds for the preparation of and/or for use in X-ray contrast media. The novel compounds possess all the properties required of X-ray contrast media. Many of these compounds, though nonionic, are very readily water-soluble. The novel compounds represent excellently compatible X-ray contrast media suitable for angiography, urography, myelography, lymphography, and for the visualization of various body cavities, and for other radiological investigations.

Due to their slight and neutral flavor, several of the compounds are highly suitable for oral administration and for introduction into the lungs for exammple compound A (malonic acid bis[3,5-bis(1,3-dihydroxyisopropylcarbamoyl)-2,4,6-triiodo-N-(2-hydroxyethyl)anilide]) and oxalic acid bis[3,5-bis(2,3-dihydroxy-propylcarbamoyl)-2,4,6-triiodo-N-(2-hydroxyethyl)anilide].

TABLE I

| | Osmotic Pressure, Viscosity, and Compatibility of Nonionic Contrast Media of Different Chemical Structure as an Aqueous Solution (Concentration: 300 mg I/ml) | | |
|---|---|---|---|
| Compound | Osmotic Pressure 37° C. (atm) | Viscosity 37° C. (cp) | LD$_{50}$ (Rat) upon i.v. Injection Rate: 2 ml/min (g Iodine/kg Body Weight) |
| A | 7.2 | 6.8 | more than 30 |
| B | 4.3 | 13.7 | 13 |
| Iopamidol | 15.7 | 4.7 | 12 |
| Metrizamide | 12.3 | 6.2 | 12 |

The bitter flavor of customary contrast media which often triggers nausea must be considered a grave disadvantage especially in gastrography and bronchography.

Consequently, the invention also concerns novel X-ray contrast media based on the compounds of Formula I. The preparation of such novel X-ray contrast media takes place in a manner known per se, for example by bringing the opacifying compound into a form suitable for intravenous administration together with the additives customary in galenic pharmacy, e.g., stabilizers, such as sodium edetate, calcium disodium edetate, physiologically compatible buffers, sodium chloride, and similar agents. The concentration of the novel X-ray contrast media in an aqueous medium is entirely dependent on the method of X-ray diagnostics employed. The preferred concentrations and dosages of the novel compounds range from 50 to 500 mg I/ml for the concentration and from 5 to 500 ml for the dosage. Concentrations of between 100 and 400 mg I/ml are especially preferred. Administration and other details of the compositions, unless indicated otherwise herein, are conventional and analogous to known X-ray contrast media such as metrizamide and iopamidol.

The present invention furthermore relates to a process for the preparation of compounds of Formula I comprising, in a conventional manner, N-hydroxyalkylating a dicarboxylic acid bis(3,5-dicarbamoyl-2,4,6-triiodoanilide) of Formula II

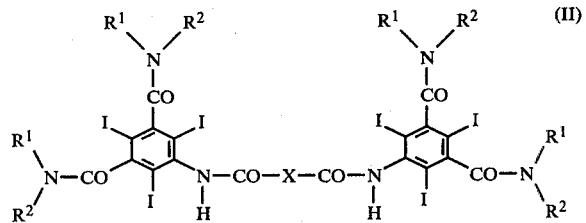

wherein
R$^1$, R$^2$, and X are as defined above and
free hydroxy groups in the molecule can be present in blocked form,
with a compound of Formula III

wherein
A is hydrogen or a CH$_2$OH-group and
B and D together represent the oxygen atom of an oxido ring or
B is hydroxy and D is chlorine, bromine sulfate or an alkyl sulfate group, and, optionally, subsequently liberating blocked hydroxy groups.

The N-alkylation of the acylated anilide groups according to this invention takes place by using conventional methods known to those skilled in the art. Thus, it is possible, for example, to react the compounds of Formula II in a suitable solvent, such as methanol, ethanol, or 1,2-propanediol, in the presence of an alkali alcoholate or alkali hydride with the compound of Formula III, for example with chloroethanol, ethylene oxide, 2,3-chloropropanediol, or glycidol (2,3-oxidopropanol) at a temperature from room temperature to 80° C., preferably 20°–50° C.

Another possibility for alkylation involves the use of the compound of Formula II with intermediarily blocked hydroxy groups. This is effected according to conventional methods by the introduction of groups which can be readily split off again, for example by etherification (e.g., introduction of the triphenylmethyl residue).

The hydroxy group blocking step can also be achieved by ketalizing or acetalizing, e.g., by means of acetaldehyde, acetone, 2,2-dimethoxypropane, or dihydropyran.

The subsequent splitting off of the intermediarily introduced blocking groups with liberation of the finally desired hydroxy groups also takes place by means of methods generally known to persons skilled in the art. Thus, the blocking groups can be split off without a separate reaction stage while processing and isolating the reaction products. However, this step can also be conducted in the usual way in a separate reaction stage. Acyl blocking groups can be split off, for example, by alkaline hydrolysis, and acetal, ketal, or ether blocking groups can be cleaved by acid hydrolysis. The starting compounds of Formula II are disclosed in DOS No. 2,628,517 (U.S. Pat. No. 4,239,747), in French Pat. No. 7,719,234, published under No. 2,355,808 (20.01.78), or in Belgian Pat. No. 856,039, or they can be obtained by methods known per se from a tetracarboxylic acid tetrachloride of Formula IV

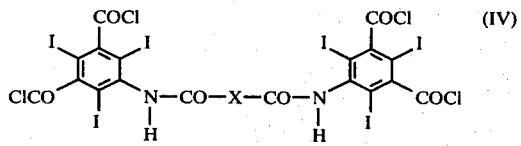

described in DOS No. 2,628,517 (U.S. Pat. No. 4,239,747) and wherein X is a defined above, by reaction with an amine

wherein $R^1$ and $R^2$ are as defined above and wherein the free hydroxy groups which can be present in $R^1$ and $R^2$ can be in blocked form.

Insofar as they are not as yet disclosed, the tetracarboxylic acid tetrachlorides of Formula IV can be prepared by conventionally reacting the 5-amino-2,4,6-triiodoisophthalic acid dichloride of Formula V

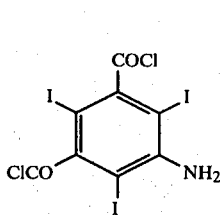

with a dicarboxylic acid chloride of Formula VI

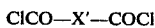

wherein
X' is as defined for X and,
additionally, any free hydroxy groups can be blocked.

Suitable blocking groups are those customarily employed, and moreover the 1,2-oxido group. This reaction is explained in greater detail below with reference to the preparation details for malonic acid bis[3,5-bis(chlorocarbonyl)-2,4,6-triiodoanilide] as follows:

A hot solution of 298 g (0.5 mole) of 5-amino-2,4,6-triiodoisophthalic acid dichloride in 650 ml of dioxane is combined dropwise at an internal temperature of 90° C. with 29 ml (0.3 mole) of malonic acid dichloride and stirred under reflux for 2 hours, during which step a thick precipitate is obtained. After stirring overnight at room temperature, the precipitate is filtered off, washed with dioxane, and dried at 50° C. under vacuum, thus obtaining 298 g (79.8% of theory) of malonic acid bis[3,5-bis(chlorocarbonyl)-2,4,6-triiodoanilide] (dioxane content 15.8%), mp 310° C. (decomposition).

The thus-prepared tetracarboxylic acid tetrachlorides of Formula IV are then reacted with an amine

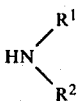

wherein $R^1$ and $R^2$ are as defined above, and wherein free hydroxy groups in $R^1$ and $R^2$ can be blocked, thus obtaining the compounds of Formula II.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Malonic Acid Bis[3,5-bis(2,3-dihydroxypropyl-N-methylcarbamoyl)-2,4,6-triiodo-N-2-hydroxyethylanilide]

(a) At 50°–60° C. under agitation, a solution of 52.5 g (500 mmol) of N-methylamino-2,3-propanediol in 150 ml of dimethylacetamide is added dropwise within 15 minutes to a solution of 150 g (100 mmol) of malonic acid bis[3,5-bis(chlorocarbonyl)-2,4,6-triiodoanilide] (dioxane content taken into account) in 250 ml of dimethylacetamide; during this step, the temperature is permitted to rise to 59° C. Within another 10 minutes, 118.8 ml (0.5 mol) of tributylamine is added to the reaction mixture. The latter is stirred for another 4 hours at 50° C. and overnight at room temperature. Then the reaction mixture is combined with 18.3 ml of concentrated hydrochloric acid to obtain an acidic reaction, and the solution is introduced dropwise into 2 l of methylene chloride. After one hour of agitation, the liquid is decanted off from the precipitate, the precipitate is again stirred for one hour with 2 l of methylene chloride, and again decanted, whereupon the precipitate is dried under vacuum at 50° C. The crude product (190 g) is dissolved in 1.5 l of water, filtered, introduced into a column with about 2 l of cation exchanger IR 120, and eluted with water. The eluate is concentrated under vacuum, dissolved in 1.5 l of water, introduced into a column with about 1.5 l of anion exchanger IRA 410, and eluted with water. This eluate is stirred for 30 minutes with 15 g of active carbon, vacuum-filtered, and concentrated under vacuum. The residue is dried at 50° C. under vacuum, thus obtaining 102 g of malonic acid bis[3,5-bis(2,3-dihydroxypropyl-N-methylcarbamoyl)-2,4,6-triiodoanilide] (66% of theory), mp 238°–240° C. (decomposition).

(b) Hydroxyethylation:

Under heating to 50° C., 3.3 g of sodium (144 mmol) is reacted in 60 ml of methanol to the methylate and finally 130 ml of 1,2-propylene glycol is added thereto. This solution is combined with 69.9 g (45 mmol) of malonic acid bis[3,5-bis(2,3-dihydroxypropyl-N-methylcarbamoyl)-2,4,6-triiodoanilide] and then, to accelerate dissolution, with 300 ml of methanol. After 15 minutes at 50° C., the solution is clear. The methanol is then distilled off under vacuum. At about 50° C., 9 ml (135 mmol) of chloroethanol is now added dropwise under vigorous agitation, and the mixture is stirred for 5 hours at 50° C. After cooling to room temperature, the slightly yellowish, turbid solution is introduced dropwise under agitation into 2 l of acetone. After one hour of agitation, the precipitate is vacuum-filtered, extracted for 30 minutes with 500 ml of acetone, again vacuum-filtered, and dried under vacuum at 50° C. The crude product is dissolved in 500 ml of water, and the solution is introduced into a column with about 500 ml of cation exchanger IR 120. After elution with water, the mixture is concentrated under vacuum to 400 ml and introduced into a column with 500 ml of anion exchanger (IRA 410). After elution with water, the eluate is stirred for 30 minutes with 4 g of carbon, vacuum-filtered, and concentrated under vacuum, thus obtaining 59.3 g of the title compound (80% of theory), mp 247°–249° C. (decomposition).

EXAMPLE 2

Oxalic Acid Bis[3,5-bis(2,3-dihydroxypropylcarbamoyl)-2,4,6-triiodo-N-(2-hydroxyethyl)anilide]

(a) At 50°–60° C. under agitation, a solution of 117 g (1.28 mol) of 1-amino-2,3-propanediol in 234 ml of dimethylacetamide is added dropwise within 30 minutes to a solution of 188 g (142 mmol) of oxalic acid bis[3,5-bis(chlorocarbonyl)-2,4,6-triiodoanilide] (dioxane content taken into account) in 376 ml of dimethylacetamide. The mixture is then further stirred for 4 hours at about 50° C. and overnight at room temperature. The solution is acidified with 15 ml of concentrated hydrochloric acid and evaporated under vacuum at 50° C. The residue is stirred into 2 l of water, agitated overnight, the precipitate is vacuum-filtered and washed with water. After drying at 50° C. under vacuum, 156 g (75% of theory) of oxalic acid bis[3,5-bis(2,3-dihydroxypropylcarbamoyl)-2,4,6-triiodoanilide] is obtained; mp: no decomposition up to 310° C.

(b) Hydroxyethylation:

Under heating to 50° C., 3 g (130 mmol) of sodium is reacted in 120 ml of methanol to the methylate, and 130 ml of 1,2-propylene glycol is added thereto. To this mixture are added 44 g (30 mmol) of oxalic acid bis[3,5-bis(2,3-dihydroxypropylcarbamoyl)-2,4,6-triiodoanilide] and, to accelerate dissolution, 300 ml of methanol. After 15 minutes at 50° C., the solution is clear. The methanol is then distilled off under vacuum, thus producing a suspension. At about 50° C., 8 ml (120 mmol) of chloroethanol is then added dropwise under vigorous agitation, and the mixture is stirred for 5 hours at 50° C. and overnight at room temperature. The turbid solution is added dropwise under stirring to 2 l of acetone, and the thus-obtained precipitate is vacuum-filtered after one hour. Then the precipitate is extracted for 30 minutes with 500 ml of acetone, vacuum-filtered, and dried under vacuum at 50° C. The crude product (51.3 g) is poured in a 10% aqueous solution over 500 ml of cation exchanger (IR 120) and eluted with water. The eluate is concentrated to about 400 ml and introduced into a column with about 500 ml of anion exchanger (IRA 410) and eluted with water. The eluate is stirred with 4 g of active carbon, vacuum-filtered, and concentrated to dryness under vacuum. To remove the residual propylene glycol and to obtain a more easily manipulatable crystallized product, the residue is extracted under boiling once to twice with respectively 130 ml of ethanol, vacuum-filtered after cooling, and dried under vacuum at 50° C., thus obtaining 25 g (56% of theory) of the title compound; mp 293°–296° C. (decomposition).

EXAMPLE 3

Oxalic Acid Bis[3,5-bis(1,3-dihydroxyisopropylcarbamoyl)-2,4,6-triiodo-N-(2-hydroxyethyl)anilide]

(a) Analogously to Example 2(a), 199 g (150 mmol) of oxalic acid bis[3,5-bis(chlorocarbonyl)-2,4,6-triiodoanilide] (dioxane content taken into account) is reacted with 123 g (1.35 mol) of 2-amino-1,3-propanediol (serinol), and worked up. The precipitate is stirred for 2 days with water, vacuum-filtered, and dried, thus producing 198 g (90% of theory) of oxalic acid bis[3,5-bis(1,3-dihydroxyisopropylcarbamoyl)-2,4,6-triiodoanilide]; mp: no decomposition up to 310° C.

(b) Hydroxyethylation:

Analogously to Example 2(b), the sodium methylate/propylene glycol solution is combined with 44 g (30 mmol) of oxalic acid bis[3,5-bis(1,3-dihydroxyisopropylcarbamoyl)-2,4,6-triiodoanilide], and methanol is added. After heating for one hour to 70° C., the methanol is distilled off under vacuum and the thus-obtained suspension is combined—as described in Example 2(b)—with 8 ml (120 mmol) of 2-chloroethanol and thereafter further processed over ion exchangers.

For purposes of further purification, the crude product (26 g) is refluxed for 16 hours with 110 ml of ethanol. After cooling, the product is filtered off and dried, thus obtaining 23 g (50% of theory) of the title compound; mp: no decomposition up to 310° C.

EXAMPLE 4

Malonic Acid
Bis[3,5-bis(2,3-dihydroxypropylcarbamoyl)-2,4,6-triiodo-N-(2-hydroxyethyl)anilide]

(a) Analogously to Example 2(a), 75 g (50 mmol) of malonic acid bis[3,5-bis(chlorocarbonyl)-2,4,6-triiodoanilide] (dioxane content taken into account) is reacted with 41 g (450 mmol) of 1-aminopropanediol and worked up. The crude product, however, is stirred with 700 ml of water for 2 days, the precipitate is vacuum-filtered, washed with water, and dried under vacuum at 50° C., thus producing 59 g (80% of theory) of malonic acid bis[3,5-bis(2,3-dihydroxypropylcarbamoyl)-2,4,6-triiodoanilide]; mp 262°–268° C. (decomposition).

(b) Hydroxyethylation:
Analogously to Example 2(b), the solution prepared from 1.5 g (65 mmol) of sodium, methanol, and 1,2-propylene glycol is combined with 22.2 g (15 mmol) of malonic acid bis[3,5-bis(2,3-dihydroxypropylcarbamoyl)-2,4,6-triiodoanilide] and diluted with 150 ml of methanol. After 2.5 hours of agitation at about 60° C., the compound has been dissolved. After the methanol has been distilled off under vacuum, the subsequently conducted hydroxyethylation with 4 ml (60 mmol) of chloroethanol yields, after working up the product over ion exchangers, refluxing with 165 ml of n-butanol instead of ethanol, and extraction with diethyl ether, as well as drying under vacuum, 15 g (64% of theory) of the title compound; mp 238° C. (decomposition).

EXAMPLE 5

Malonic Acid
Bis[3,5-bis(1,3-dihydroxyisopropylcarbamoyl)-2,4,6-triiodo-N-(2-hydroxyethyl)anilide]

(a) Analogously to Example 2(a), 252 g (192 mmol) of malonic acid bis[3,5-bis(chlorocarbonyl)-2,4,6-triiodoanilide] (dioxane content taken into account) is reacted with 164 g (1.8 mol) of 2-amino-1,3-propanediol (serinol) and worked up. However, the crude product is agitated for 2 days with only 1 liter of water, thus obtaining 226 g (79.5% of theory) of malonic acid bis[3,5-bis(1,3-dihydroxyisopropylcarbamoyl)-2,4,6-triiodoanilide]; mp 289°–298° C. (decomposition).

(b) Hydroxyethylation:
Analogously to Example 2(b), the sodium methylate/propylene glycol solution from 15.6 g (680 mmol) of sodium is combined with 236.6 g (157 mmol) of malonic acid bis[3,5-bis(1,3-dihydroxyisopropylcarbamoyl)-2,4,6-triiodoanilide] and diluted with 1 liter of methanol. After preparing a solution and distilling off the methanol under vacuum, 42 ml (628 mmol) of 2-chloroethanol is added thereto. The usual working-up process yields, after boiling extraction with 800 ml of ethanol, 147 g (60% of theory) of the title compound; mp 300° C.

EXAMPLE 6

Oxalic Acid
Bis[3,5-bis(2,3-dihydroxypropyl-N-methylcarbamoyl)-2,4,6-triiodo-N-(2-hydroxyethyl)anilide]

Analogously to Example 2(b), the sodium methylate/1,2-propylene glycol solution (prepared from 1.1 g—48 mmol—of sodium) is combined with a solution of 23.3 g (15 mmol) of oxalic acid bis[3,5-bis(2,3-dihydroxypropyl-N-methylcarbamoyl)-2,4,6-triiodoanilide] and, after removing the methanol by distillation under vacuum, reacted with 3 ml (45 mmol) of chloroethanol. After treatment with ion exchangers and purification with active carbon, evaporation yields 17.4 g (72% of theory) of the title compound; mp 257°–259° C. (decomposition).

EXAMPLE 7

3,6-Dioxasuberic Acid
Bis[3,5-bis(1,3-dihydroxyisopropylcarbamoyl)-2,4,6-triiodo-N-(2-hydroxyethyl)anilide]

(a) Analogously to Example 2(a), 34.1 g (24 mmol) of 3,6-dioxasuberic acid bis[3,5-bis(chlorocarbonyl)-2,4,6-triiodoanilide] (dioxane content taken into account), dissolved in 68 ml of dimethylacetamide, is reacted with a solution of 19.9 g (219 mmol) of 2-amino-1,3-propanediol (serinol) in 60 ml of dimethylacetamide. After acidifying and concentrating the reaction mixture, the residue is treated—according to Example 1(a)—with ion exchangers. Working up yields 20.7 g (13.3 mmol) of 3,6-dioxasuberic acid bis[3,5-bis(1,3-dihydroxyisopropylcarbamoyl)-2,4,6-triiodoanilide]; mp: no decomposition up to 310° C.

(b) Hydroxyethylation:
Analogously to Example 2(b), the sodium methylate/1,2-propylene glycol solution (prepared from 1.02 g—44.3 mmol—of sodium) is combined with 16.3 g (10.3 mmol) of 3,6-dioxasuberic acid bis[3,5-bis(1,3-dihydroxyisopropylcarbamoyl)-2,4,6-triiodoanilide] and diluted with 50 ml of methanol. After preparing a solution and removing the methanol by distillation under vacuum, 2.8 ml (41.2 mmol) of chloroethanol is added. Working up and extraction under boiling with 60 ml of ethanol yields 11.3 g (67% of theory) of the title compound; mp 251°–265° C. (decomposition).

EXAMPLE 8

Malonic Acid
Bis[3,5-bis(bis-2-hydroxyethylcarbamoyl)-2,4,6-triiodo-N-(2-hydroxyethyl)anilide]

(a) Analogously to Example 2(a), 131 g (100 mmol) of malonic acid bis[3,5-bis(chlorocarbonyl)-2,4,6-triiodoanilide] (dioxane content taken into account) is reacted with 94.5 g (900 mmol) of diethanolamine and worked up. However, the residue is stirred together with only 1 liter of water. Yield: 114 g (75% of theory) of malonic acid bis[3,5-bis(bis-2-hydroxyethylcarbamoyl)-2,4,6-triiodoanilide]; mp 235°–244° C. (decomposition).

(b) Hydroxyethylation:
Analogously to Example 2(b), the sodium methylate/1,2-propylene glycol solution (prepared from 4.94 g—215 mmol—of sodium) is combined with 76.7 g (50 mmol) of malonic acid bis[3,5-bis(bis-2-hydroxyethylcarbamoyl)-2,4,6-triiodoanilide], and the mixture is diluted with methanol. After preparing a solution and removing the methanol by vacuum distillation, 13.4 ml (200 mmol) of 2-chloroethanol is added. After working up of the reaction mixture and desalting same over ion exchangers—according to Example 2(b)—the crude product is made to crystallize by boiling for 16 hours in 350 ml of ethanol, thus obtaining 61.3 g (75.7% of theory) of the title compound; mp 249°–258° C. (decomposition).

EXAMPLE 9

Preparation of a Ready-For-Use Solution:

Malonic acid bis[3,5-bis(1,3-dihydroxyisopropylcarbamoyl)-2,4,6-triiodo-N-(2-hydroxyethyl)anilide]: 617.08 g
Calcium disodium edetate: 0.10 g
Sodium bicarbonate: 1.08 g
Aqua bidestillata to make: 1000 ml The opacifying compound is dissolved in some Aqua bidestillata after adding calcium disodium edetate, and the pH of the solution is brought to 7 by adding sodium carbonate. After the volume has been brought to 1000 ml by adding Aqua bidestillata, the solution is then heat-sterilized. The iodine content is 300 mg/ml.

EXAMPLE 10

Malonic Acid Bis[3,5-bis(2,3-dihydroxy-1-hydroxymethylpropylcarbamoyl)-2,4,6-triiodo-N-(2-hydroxyethyl)anilide]

(a) Analogously to Example 1(a), 131 g (100 mmol) of malonic acid bis[3,5-bis(chlorocarbonyl)-2,4,6-triiodoanilide] (dioxane content taken into account) is reacted with 72.5 g (450 mmol) of 6-amino-2,2-dimethyl-1,3-dioxepin-5-ol or with 55.4 g of 1,2,4-trihydroxy-3-aminobutane in the presence of 107 ml (450 mmol) of tributylamine and worked up, thus obtaining 116 g (73% of theory) of malonic acid bis[3,5-bis-(2,3-dihydroxy-1-hydroxymethylpropylcarbamoyl)-2,4,6-triiodoanilide]; mp 254°–263° C. (decomposition).

(b) Hydroxyethylation:

A solution of sodium methylate (prepared from 4.94 g of sodium) in 200 ml of methanol and 215 ml of 1,2-propylene glycol is combined at 50° C. with 79.9 g (50 mmol) of malonic acid bis[3,5-bis(2,3-dihydroxy-1-hydroxymethylpropyl)-2,4,6-triiodoanilide]. After 15 minutes, the solution is freed of methanol under vacuum, combined at 50° C. under vigorous agitation with 13.4 ml (200 mmol) of chloroethanol, maintained for 5 hours at this temperature, and further stirred overnight without heating. The usual working up step by precipitation with acetone and desalting over ion exchangers yields an evaporation residue which crystallizes by boiling with 350 ml of ethanol. Yield of title compound: 55.5 g (61.2% of theory); mp 245°–257° C. (decomposition).

EXAMPLE 11

Malonic Acid Bis[3,5-bis(1,3-dihydroxyisopropylcarbamoyl)-2,4,6-triiodo-N-(2,3-dihydroxypropyl)anilide]

A solution of sodium methylate (produced from 4.94 g of sodium) in 300 ml of methanol and 215 ml of 1,2-propylene glycol is combined at 50° C. with 75.1 g (50 mmol) of malonic acid bis[3,5-bis(1,3-dihydroxyisopropylcarbamoyl)-2,4,6-triiodoanilide]. After 15 minutes, the solution is freed of methanol under vacuum, combined at 50° C. under vigorous agitation with 16.7 ml (200 mmol) of 3-chloropropanediol, maintained at this temperature for 5 hours, and further stirred overnight without heating. Usual working up of the reaction mixture by precipitation with acetone and desalting over ion exchangers according to Example 2(b) yields an evaporation residue which is crystallized by boiling with 350 ml of isopropanol. Yield of title compound: 50.7 g (62.3% of theory); mp 229°–242° C. (decomposition).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An N-Hydroxyalkylated dicarboxylic acid bis (3,5-dicarbamoyl-2,4,6-triiodoanilide) of the formula

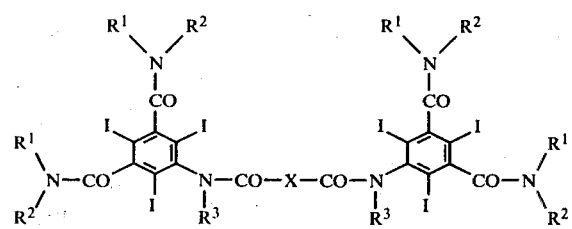

wherein
$R^1$ is $C_{2-8}$-, mono- or polyhydroxyalkyl,
$R^2$ is hydrogen, $C_{1-4}$-alkyl, or $R^1$,
$R^3$ is $C_{2-3}$-mono- or dihydroxyalkyl, and
X is a direct bond or linear or branched alkylene of 1–6 C-atoms, optionally interrupted by 1–3 oxa atoms separated from each other by at least two methylene groups and from the ends of the alkylene group by at least one methylene group or substituted by 1–4 hydroxy or $C_{1-2}$-alkoxy groups.

2. Malonic acid bis[3,5-bis(1,3-dihydroxyisopropylcarbamoyl)-2,4,6-triiodo-N-2-hydroxyethylanilide], a compound of claim 1.

3. Malonic acid bis[3,5-bis(2,3-dihydroxypropyl-N-methylcarbamoyl)-2,4,6-triiodo-N-2-hydroxyethylanilide], a compound of claim 1.

4. Malonic acid bis[3,5-bis(2,3-dihydroxy-1-hydroxymethylpropylcarbamoyl)-2,3,6-triiodo-N-2-hydroxyethylanilide], a compound of claim 1.

5. Oxalic acid bis[3,5-bis(1,3-dihydroxyisopropylcarbamoyl)-2,4,6-triiodo-N-2-hydroxyethylanilide], a compound of claim 1.

6. Oxalic acid bis[3,5-bis(2,3-dihydroxypropyl-N-methylcarbamoyl)-2,4,6-triiodo-N-2-hydroxyethylanilide], a compound of claim 1.

7. 3,6-Dioxasuberic acid bis[3,5-bis(1,3-dihydroxyisopropylcarbamoyl)-2,4,6-triiodo-N-2-hydroxyethylanilide], a compound of claim 1.

8. A compound of claim 1 wherein $R^1$ has 2–5 C-atoms and 1–5 OH groups; $R^2$ is of 1 or 2 C-atoms; and X is of 1–4 C-atoms, optionally substituted by OH or interrupted by 1–3 oxa atoms.

9. A compound of claim 1 wherein $R^1$ is straight chain alkyl of 2–4 carbon atoms or branched alkyl of 3–5 carbon atoms and the number of OH groups therein is 1–3; $R^2$ is methyl; $R^3$ is hydroxyethyl; and X is straight chain alkylene of 1–4 C-atoms.

10. A pharmaceutical composition for use in X-ray diagnostic testing comprising an amount of a compound of claim 1 effective as an X-ray contrast agent and a pharmaceutically acceptable carrier.

11. A composition of claim 10, wherein the concentration of X-ray contrast agent is 50–500 mg I/ml.

12. A method of conducting X-ray diagnostic testing in a patient in need of the same comprising administering an X-ray contrast agent of claim 1 to the patient and then subjecting the patient to X-ray radiation.

13. Malonic Acid Bis[3,5-bis(1,3-dihydroxyisopropylcarbamoyl)-2,4,6-triiodo-N-(2,3-dihydroxypropyl)-anilide], a compound of claim 1.

14. A compound of claim 1 wherein $R^2$ is H or $R^1$ and X is a direct bond or $C_{1-4}$-alkylene.

15. A compound of claim 1 wherein $R^2$ is H or $R^1$ and X is a direct bond or methylene.

16. A compound of claim 1 wherein X is $C_{1-6}$-alkylene.

17. A compound of claim 1 wherein X is $C_{1-4}$-alkylene.

18. A compound of claim 1 wherein X is $-CH_2-$.

19. A compound of claim 1 wherein X is $C_{1-6}$-alkylene or $C_{1-6}$-alkylene substituted by 1-4 hydroxy or $C_{1-2}$-alkoxy groups.

* * * * *